United States Patent [19]
Baumann et al.

[11] 3,971,808
[45] July 27, 1976

[54] SPIRODIPYRANS AND CHROMOGENIC MATERIALS FOR COPYING PROCESSES

[75] Inventors: Hans Baumann; Andreas Oberlinner, both of Ludwigshafen, Germany

[73] Assignee: BASF Aktiengesellschaft, Ludwigshafen (Rhine), Germany

[22] Filed: May 7, 1974

[21] Appl. No.: 467,829

[30] Foreign Application Priority Data
May 11, 1973 Germany............................ 2323803

[52] U.S. Cl.................................. 260/345.2; 8/7; 260/571; 260/576
[51] Int. Cl.²........................................ C07D 311/02
[58] Field of Search................................. 260/345.2

[56] References Cited
UNITED STATES PATENTS

| | | | |
|---|---|---|---|
| 2,978,462 | 4/1961 | Berman et al. | 260/345.2 |
| 3,022,318 | 2/1962 | Berman et al. | 260/345.2 |
| 3,666,525 | 5/1972 | Kimura et al. | 260/345.2 |

*Primary Examiner*—James O. Thomas, Jr.
*Assistant Examiner*—Nicky Chan
*Attorney, Agent, or Firm*—Johnston, Keil, Thompson & Shurtleff

[57] ABSTRACT

Spirodipyrans based on condensed pyrylium salts and 4-dialkylamino-2-hydroxybenzaldehydes, their manufacture and their use as chromogenic materials in pressure-sensitive recording materials, particularly copying papers.

6 Claims, No Drawings

SPIRODIPYRANS AND CHROMOGENIC MATERIALS FOR COPYING PROCESSES

This invention relates to spirodipyrans of formula I

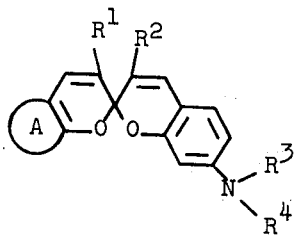

in which
- A denotes a benzene or naphthalene nucleus optionally monosubstituted or polysubstituted by chlorine, bromine, alkoxy or carboxylic ester,
- $R^1$ denotes a benzene nucleus optionally mono- or poly-substituted by chlorine, bromine, alkyl or nitro,
- $R^2$ denotes hydrogen or alkyl or aryl both of from 1 to 8 carbons and
- $R^3$ and $R^4$ denote a $C_{1-6}$ alkyl radical optionally substituted by cyano.

More particularly, it relates to spirodipyrans of formula Ia

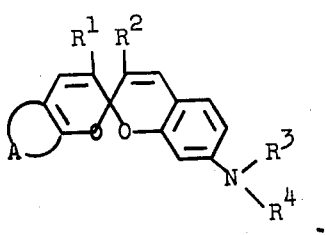

in which
A is

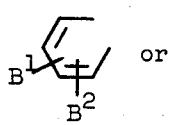 or 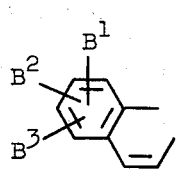

wherein $B^1$, $B^2$ and $B^3$ each individually denotes hydrogen, chlorine, bromine, methoxy, ethoxy or carboalkoxy containing $C_{1-4}$ alkoxy,

- $R^1$ is phenyl or phenyl substituted by chlorine, bromine, nitro or $C_{1-4}$ alkyl,
- $R^2$ is hydrogen, $C_{1-8}$ alkyl or phenyl and
- $R^3$ and $R^4$ are $C_{1-6}$ alkyl or cyanoalkyl of from 2 to 6 carbon atoms.

The spirodipyrans of formula I are compounds having little or no color. When dissolved in non-polar or weakly polar solvents such as hydrocarbons, chlorohydrocarbons and esters, they give intense blue colorations when acid substances are added. This reaction, which is also caused by kaolin, zeolites, bentonite, silicic acid and phenolic condensation products, makes the compounds suitable for use as dye precursors in pressure-sensitive recording materials, particularly copying papers.

Preferred values of $R^2$ are, in addition to hydrogen, methyl, ethyl and phenyl. Of particular industrial significance are the compounds of the formulae:

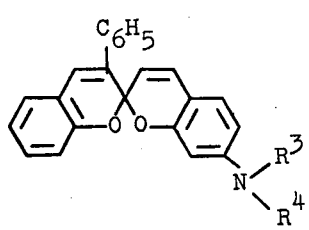

and

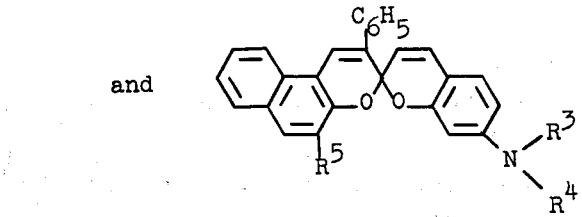

wherein the substituent $R^5$ denotes hydrogen or a $-COOCH_3$ or $-COOC_2H_5$ group.

Suitable values of $R^3$ and $R^4$, which are preferably the same, are methyl, ethyl, propyl and β-cyanoethyl.

The spirodipyrans of formula I may be prepared by condensation of 2-alkyl-3-arylbenzopyrylium salts or 2-alkyl-3-arylnaphthopyrylium salts (compounds of formula II) or the corresponding β-(2-hydroxyaryl-1)vinyl ketones (compounds of formula III) with 4-dialkylamino-2-hydroxybenzaldehydes (compounds of formula IV) or from β-(2-hydroxy-4-dialkylaminoaryl-1)vinyl ketones (compounds of formula VI) and o-hydroxyaldehydes (compounds of formula V) according to the following schemes in conventional manner:

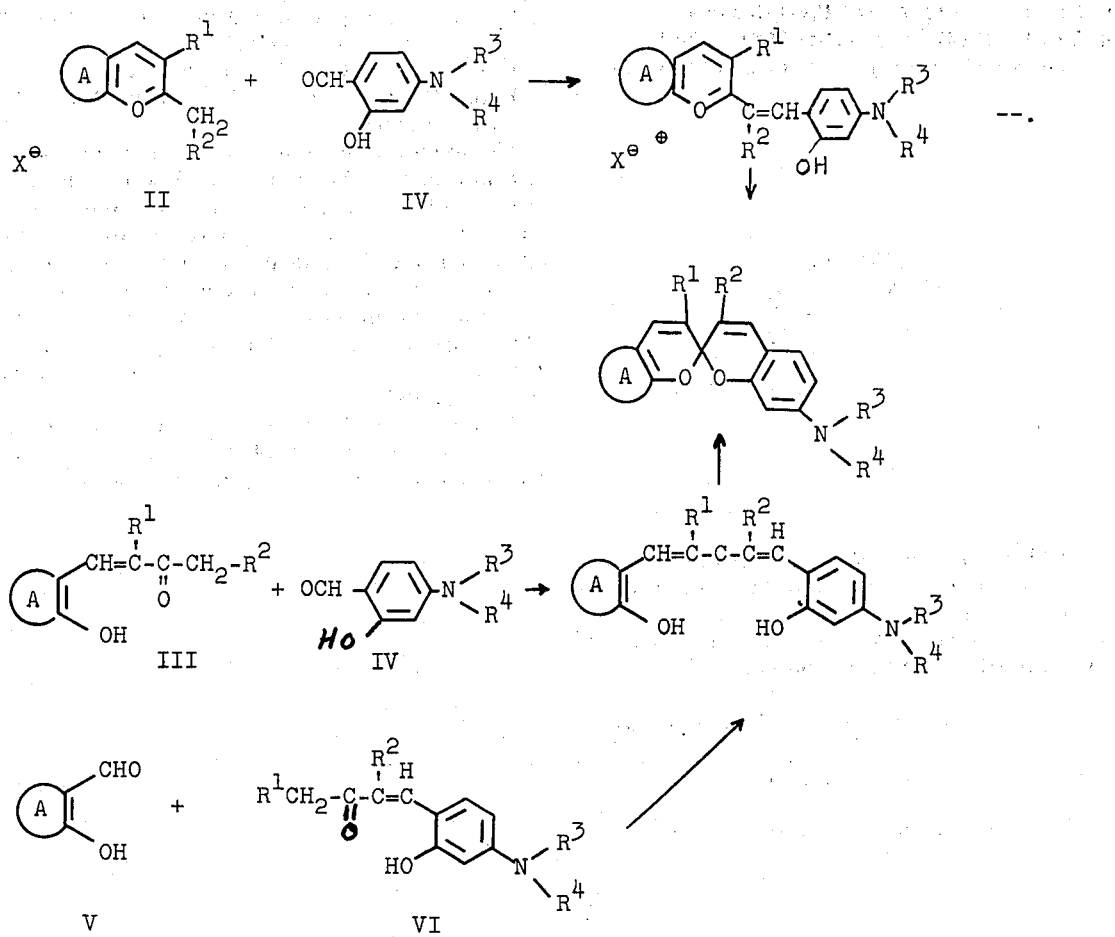

Specific examples of suitable starting materials are as follows:

Pyrylium salts of formula II in the form of their chlorides, perchlorates, tetrafluoroborates, tetrachloroferrates or trichlorozincates
  2-methyl-3-phenylbenzopyrylium salt
  2-methyl-3-phenylnaphtho-[2,1-b]-pyrylium salt
  2-methyl-3-phenyl-10-carbomethoxynaphtho-[2,1-b]-pyrylium salt
  2-benzyl-3-phenylbenzopyrylium salt
  2-benzyl-3-phenylnaphtho-[2,1-b]-pyrylium salt
  2-methyl-3-phenyl-6-bromo-benzopyrylium salt
  2-ethyl-3-phenylbenzopyrylium salt.

Aldehydes of formula IV
  4-dimethylamino-2-hydroxybenzaldehyde
  4-diethylamino-2-hydroxybenzaldehyde
  4-(N-methyl-N-β-cyanoethylamino)-2-hydroxybenzaldehyde.

β-(2-Hydroxyaryl-1)-vinyl ketones of formula III
  methyl-(2-hydroxy-α-phenylstyryl) ketone
  ethyl-(2-hydroxy-α-phenylstyryl) ketone
  benzyl-(2-hydroxy-α-phenylstyryl) ketone
  methyl-(2-hydroxy-5-bromo-α-phenylstyryl) ketone
  β-(2-hydroxynaphthyl-1)α-phenylvinyl ketone.

Compounds of formula V
  salicylaldehyde
  2-hydroxy-5-bromobenzaldehyde
  2-hydroxy-5-chlorobenzaldehyde
  β-oxynaphthaldehyde
  2-hydroxy-3-carbomethoxy-1-naphthaldehyde
  2-hydroxy-3-carboethoxy-1-naphthaldehyde.

Compounds of formula VI
  benzyl-(2-hydroxy-4-dimethylamino-styryl) ketone
  benzyl-(2-hydroxy-4-diethylamino-styryl) ketone
  benzyl-[2-hydroxy-4-(N-methyl-N-β-cyanoethyl)-styryl]ketone
  benzyl-(2-hydroxy-4-dimethylamino-α-methyl-styryl) ketone
  benzyl-(2-hydroxy-4-diethylamino-α-methyl-styryl) ketone
  benzyl-(2-hydroxy-4-diethylamino-α-phenyl-styryl ketone.

The condensation is conveniently carried out in organic solvents which are liquid at the temperature of the reaction, for example alcohols, carboxylic acids, carboxylic anhydrides, carboxamides, hydrocarbons and acetonitrile, in the presence or absence of acidic or basic condensing agents such as zinc chloride, phosphoric acid, toluenesulfonic acid, boric acid, pyridine, piperidine, triethylamine and ammonium acetate, in amounts as usually used for condensation reactions of this kind and under the usual condensation conditions. Advantageously, condensation is carried out at temperatures ranging from 20° to 120°C. The ring closure to the pyran may take place at the same time as or subsequently to the condensation in the same or a separate stage, optionally in the presence of bases such as sodium or potassium hydroxide or carbonate, sodium acetate, ammonia, aliphatic amines and pyridine, in conventional manner. The crystallized spirodipyran compounds precipitated from the solution may then be used in known manner as dye precursors in copying processes.

For example, they may be worked into a paste which is then coated onto paper and overcoated with a protective layer. A particularly advantageous method is to use the dye precursors in solution in a non-volatile or high-boiling solvent such as chloroparaffin trichlorodiphenyl or one of the usual solvents such as toluene, and to encapsulate the solution in microcapsules, with which the paper surface is then coated. When this layer is pressed (for example by a writing operation) against a surface which has been coated with an acid reacting substance, blue designs (e.g. characters) are formed. The solutions of the 3'-arylspirodipyranes of the invention show virtually no coloration when applied to normal paper. Thus no mirror image is produced on the reverse side of the top sheet coated with the dye precursor during the copying operation. In addition to this advantage, the spirodipyrans of the invention give characters which are distinguished by particularly high strength and good photocopying properties.

In the following Examples the parts and percentages are by weight.

EXAMPLE 1

126 parts of 2-methyl-3-phenylbenzopyrylium tetrachloroferrate and 65 parts of diethylaminosalicylaldehyde are heated for 2 hours under reflux in 900 parts of alcohol. When condensation is complete, the solvent is decanted and the dye is stirred in 100 parts of 25% ammonia solution and 1,000 parts of benzene until it loses its color completely. The benzene phase is separated, purified with animal charcoal, dried over sodium sulfate and concentrated to a volume of about 300 parts. 150 parts of ligroin are added to this solution to precipitate 74 parts of 3'-phenyl-7-diethylamino-2,2'-spiro-di-[2H-1-benzopyran] in the form of pale yellow crystals. The melting point of this compound is 140°–142°C.

When a solution of this compound in dodecylbenzene is enclosed in microcapsules, which are then coated onto the surface of paper, a blue coloration is obtained, by a writing operation, when the capsules are broken and their contents come into contact with an acid reacting layer.

EXAMPLE 2

42 parts of 2-methyl-3-phenylbenzopyrylium tetrachloroferrate and 20 parts of dimethylaminosalicylaldehyde are heated for 2 hours under reflux in 400 parts of alcohol. The 3'-phenyl-7-dimethylamino-2,2'-spiro-di-[2H-1-benzopyran] obtained after working up as in Example 1 has a melting point of 157–159°C.

Papers coated with this compound in microcapsules give a blue coloration when broken against an acid reacting layer by a writing operation.

EXAMPLE 3

94 parts of 2-methyl-3-phenylnaphthopyrylium tetrachloroferrate and 43 parts of diethylaminosalicylaldehyde are heated in 800 parts of alcohol for 2 hours under reflux. The dye thus formed is converted to the colorless compound 3'-phenyl-7-diethylaminospiro-[2H-1-benzopyran-2,2'-(2H)-naphtho-(2,1-b)-pyran] in the manner described in Example 1. The yield is 54 parts and the melting point of the compound is 232°–234°C.

When contacted with acid reacting substances, this compound gives a blue coloration.

EXAMPLE 4

47 parts of 2-methyl-3-phenylnaphthopyrylium tetrachloroferrate and 20 parts of dimethylaminosalicylaldehyde are heated for 2 hours under reflux in 400 parts of alcohol. The dye thus formed is converted to the colorless compound 3'-phenyl-7-dimethylamino-spiro-[2H-1-benzopyran-2,2'-(2H)-naphtho-(2,1-b)-pyran] in the manner described in Example 1, the melting point of this compound being 250°–252°C.

The yield is 21 parts. When contacted with acid reacting substances, this compound gives a blue coloration.

EXAMPLE 5

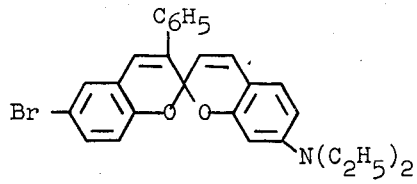

3'-phenyl-6'-bromo-7-diethylamino-2,2'-spiro-di-[2H-1-benzopyran].

EXAMPLE 6

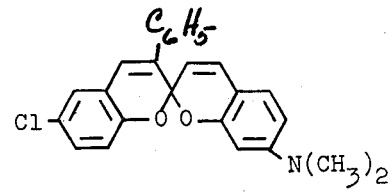

3'-phenyl-6'-chloro-7-dimethylamino-2,2'-spiro-di-[2H-1-benzopyran].

EXAMPLE 7

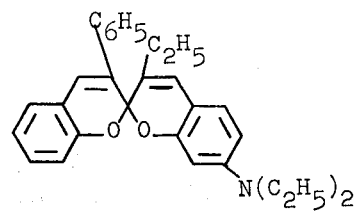

3-ethyl-3'-phenyl-7-diethylamino-2,2'-spiro-di-[2H-1-benzopyran].

EXAMPLE 8

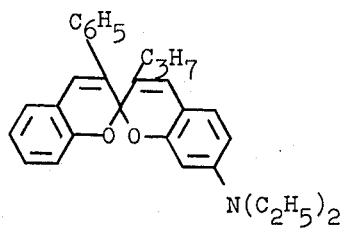

3-propyl-3'-phenyl-7-diethylamino-2,2'-spiro-di-[2H-1-benzopyran].

EXAMPLE 9

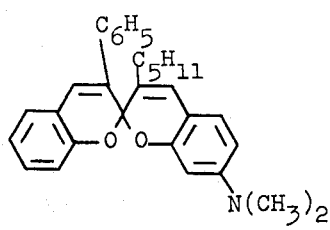

3-pentyl-3'-phenyl-7-dimethylamino-2,2'-spiro-di-[2H-1-benzopyran].

EXAMPLE 10

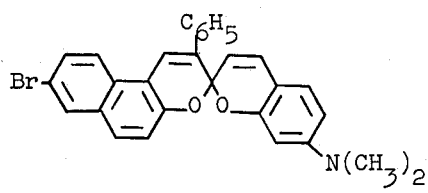

3'-phenyl-7'-bromo-7-dimethylamino-2,2'-spiro-[2H-1-benzopyran]-2,2'-(2H)-naphtho-(2,1-b)-pyran.

EXAMPLE 11

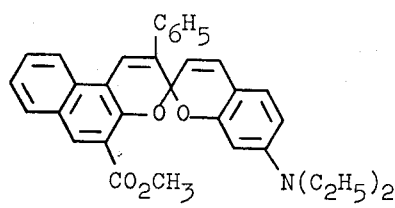

3'-phenyl-10'-carbomethoxy-7-diethylamino-spiro[2H-1-benzopyran-2,2'-(2H)-naphtho-(2,1-b)-pyran].

EXAMPLE 12

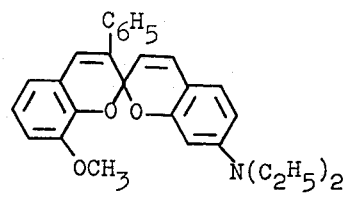

3'-phenyl-8'-methoxy-7-diethylamino-2,2'-spiro-di-[2H-1-benzopyran].

EXAMPLE 13

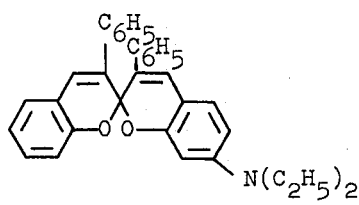

3,3'-diphenyl-7-diethylamino-2,2'-spiro-di-[2H-1-benzopyran].

EXAMPLE 14

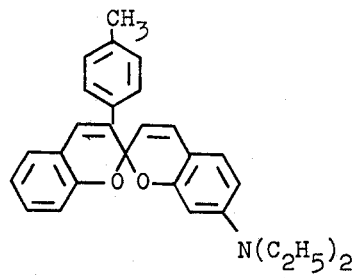

3'-(p-tolyl)-7-diethylamino-2,2'-spiro-di-[2H-1-benzopyran].

We claim:
1. A spirodipyran of the formula

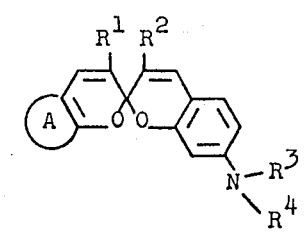

in which
A is an unsubstituted benzene or (2,1-b)-naphthalene nucleus, or a benzene or a (2,1-b)-naphthalene nucleus substituted by one chloro, bromo, methoxy, ethoxy or carbalkoxy containing a $C_1$ to $C_4$ alkoxy,
$R^1$ is phenyl, phenyl substituted by chloro, bromo or alkyl of from 1 to 4 carbon atoms,
$R^2$ is hydrogen, alkyl of from 1 to 8 carbon atoms or phenyl, and
$R^3$ and $R^4$ are methyl, ethyl or propyl.

2. A spirodipyran as claimed in claim 1 of the formula

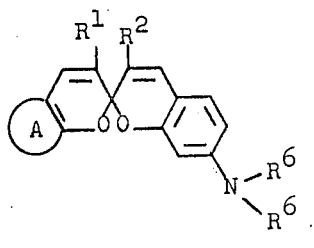

in which
 A is a benzene or a (2,1-b)-naphthalene nucleus, or a benzene or a (2,1-b)-naphthalene nucleus substituted by one chloro, bromo, methoxy, ethoxy, carbomethoxy or carboethoxy,
 $R^1$ is phenyl or methylphenyl,
 $R^2$ is hydrogen, phenyl or alkyl of from 1 to 8 carbon atoms and
 $R^6$ is methyl or ethyl.

3. A spirodipyran as claimed in claim 2, wherein $R^2$ is hydrogen, methyl, ethyl or phenyl.

4. A spirodipyran as claimed in claim 1 of the formula

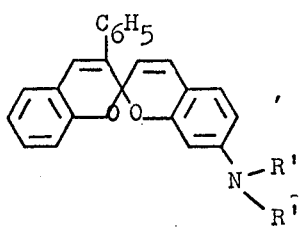

wherein R' is methyl or ethyl.

5. A spirodipyran as claimed in claim 1 of the formula

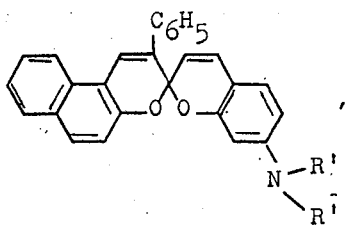

wherein R' is methyl or ethyl.

6. A spirodipyran as claimed in claim 1 of the formula

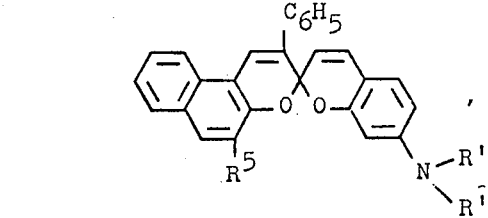

wherein $R^5$ is hydrogen, carbomethoxy or carboethoxy and R' is methyl or ethyl.

* * * * *